(12) United States Patent
Hide et al.

(10) Patent No.: US 8,129,507 B2
(45) Date of Patent: Mar. 6, 2012

(54) ATOPIC DERMATITIS INDUCER

(75) Inventors: Michihiro Hide, Hiroshima (JP);
Toshihiko Tanaka, Hiroshima (JP);
Akio Tanaka, Hiroshima (JP); Kaori Ishii, Hiroshima (JP); Hidenori Suzuki, Hiroshima (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 12/461,368

(22) Filed: Aug. 10, 2009

(65) Prior Publication Data

US 2010/0080854 A1 Apr. 1, 2010

Related U.S. Application Data

(62) Division of application No. 10/563,795, filed as application No. PCT/JP2004/010144 on Jul. 9, 2004, now abandoned.

(30) Foreign Application Priority Data

Jul. 9, 2003 (JP) .................................. 2003-194642

(51) Int. Cl.
*A23J 1/00* (2006.01)
*C07K 1/00* (2006.01)
*C07K 14/00* (2006.01)
*C07K 16/00* (2006.01)
*C07K 17/00* (2006.01)

(52) U.S. Cl. ........ 530/412; 530/414; 530/415; 530/416; 530/417

(58) Field of Classification Search .................. None
See application file for complete search history.

(56) References Cited

U.S. PATENT DOCUMENTS 5,834,192 A 11/1998 Akerblom et al.

FOREIGN PATENT DOCUMENTS

| WO | 98/11136 | 3/1998 |
|---|---|---|
| WO | 02/100895 | 12/2002 |
| WO | 03/018754 | 3/2003 |
| WO | 2004/028479 | 4/2004 |

OTHER PUBLICATIONS

Saraymen et al. 'Sweat Copper, Zinc, Iron, Magnesium, and Chrominum levels in National Wrestler.' Inonu Universitesi Tip Fakultesi Dergisi. 11(1):7-10, 2004.*
Schedle et al. 'Response of L-929 fibroblasts, human gingival fibroblasts, and human tissue mast cells to various metal cations.' J. Dent Res. 74(8):1513-1520, 1995.*
B. Schittek et al., "Dermcidin: A Novel Human Antibiotic Peptide Secreted by Sweat Glands", Nature Immunology, vol. 2, No. 12, pp. 1133-1137, Dec. 2001.
K. Sagawa et al., "Production and characterization of a monoclonal antibody for sweat-specific protein and its application for sweat identification", Int. J. Legal Med., vol. 117, No. 2, pp. 90-95, 2003.
T. Flad et al., "Detection of dermcidin-derived peptides in sweat by ProteinChip® Technology", Journal of Immunological Methods, vol. 270, No. 1, pp. 53-62, 2002.
M. Hide et al., "IgE-Mediated Hypersensitivity Against Human Sweat Antigen in Patients with Atopic Dermatitis", Acta. Dermato-Venerologica, vol. 82, pp. 335-340, 2002.

* cited by examiner

*Primary Examiner* — Nora Rooney
(74) *Attorney, Agent, or Firm* — Wenderoth, Lind & Ponack, L.L.P.

(57) ABSTRACT

An atopic dermatitis inducer binding to a human own IgE antibody and activating mast cells and basophiles, which includes a purified human secretion fraction, or an antigenic molecule or an antigenic determinant in the purified fraction, and obtained through the following steps of: filtering a human secretion, removing insoluble matters and collecting the filtrate; mixing the filtrate with a ConA-affinity carrier and collecting the supernatant; and separating a component having a histamine-releasing activity from the supernatant by column chromatography. This inducer is effective in diagnosing and treating human atopic dermatitis.

2 Claims, 8 Drawing Sheets

SEQUENCE LISTING

<160> NUMBER OF SEQ ID NOS: 2

<210> SEQ ID NO 1
<211> LENGTH: 14
<212> TYPE: PRT
<213> ORGANISM: Homo sapiens
<220> FEATURE:
<223> OTHER INFORMATION: Oligopeptide of Dermcidin

<400> SEQUENCE: 1

Leu Gly Lys Asp Ala Val Glu Asp Leu Glu Ser Val Gly Lys
1               5                   10

<210> SEQ ID NO 2
<211> LENGTH: 11
<212> TYPE: PRT
<213> ORGANISM: Homo sapiens
<220> FEATURE:
<223> OTHER INFORMATION: Oligopeptide of Dermcidin

<400> SEQUENCE: 2

Asp Ala Val Glu Asp Leu Glu Ser Val Gly Lys
1               5                   10

ATOPIC DERMATITIS INDUCER

This application is a divisional of Ser. No. 10/563,795, filed Feb. 21, 2006, now abandoned, which is a 371 U.S. national stage of International Application No. PCT/JP04/10144 filed Jul. 9, 2004, herein incorporated by reference in their entirety. This application hereby claims the date of priority under the International Convention of Japanese Patent Application No. 2003-194642, filed Jul. 9, 2003, as acknowledged in the Declaration of this application.

TECHNICAL FIELD

The invention of this application relates to an atopic dermatitis inducer (hereinafter sometimes referred to as "inducer") secreted by a patient with atopic dermatitis of his or her own, a method of diagnosing atopic dermatitis using this inducer or an antibody against the inducer, and a drug for desensitization therapy of atopic dermatitis containing this inducer as an active ingredient.

BACKGROUND ART

In recent years, the number of patients with atopic dermatitis is rapidly increasing and the ratio of the patients with atopic dermatitis to the patients who see a dermatologist exceeds 30%, and it becomes one of the major dermatitis. Atopic dermatitis is one of the atopic diseases caused by a hereditary factor that readily produces an IgE antibody against a common allergen, in addition to various environmental factors. The disease starts in infancy and runs a course of disease chronically with age, and becomes milder before puberty in many cases. However, in some cases, the disease continues to persist after puberty, and also there are some cases where the disease starts after puberty. Most of the adult cases are particularly intractable, and it is difficult to expect that the disease may go into outgrow with age thereafter. The completed lesions are lichenified, pruritus is severe, which is often spasmodic, and the disease runs a course of exacerbation and remission associated with other atopic diseases to a certain degree.

Much of the pathogenesis of such atopic dermatitis still remains to be clarified, there is still a problem of distinguish the atopic dermatitis from other skin diseases, and the therapeutic method has not been established yet. Conventionally, external use of an adrenal corticosteroid, medication of an antihistamine or a chemical mediator release inhibitor, a dietary therapy in which egg, milk, soybean or the like is eliminated from the cooking ingredients, elimination of antigens such as mites, fungi (mold) and the like from the living environment and the like have been attempted. However, in the case of the medication, since the drug is intended to be used in a child growing up and over a long period of time, there remains a problem of a side effect. In addition, in the dietary therapy or the measures for eliminating antigens in the environment, it is difficult to completely eliminate the antigens, and also there is a problem of a heavy mental burden.

In view of such circumstances, recently, a study in which while the pathogenesis of atopic dermatitis is being elucidated by making full use of the molecular biological knowledge, a therapeutic effect is going to be improved by inhibiting part of its pathogenesis has been conducted. For example, by focusing on the fact that the production of an IgE antibody against an antigen is part of the mechanism of developing the symptoms as described above, a method of alleviating the symptoms by externally applying a substance inhibiting the production of an IgE antibody against an antigen has been proposed (Patent Documents 1 to 3).

In addition, the present inventors have reported on purification and analysis of an antigen contained in sweat in Non-Patent Document 1. In addition, the present inventors have filed a patent application for the invention entitled "atopic dermatitis inducing proteins" (Patent Document 4).

Patent Document 1: JP-A-7-109290
Patent Document 2: JP-A-7-109292
Patent Document 3: JP-A-9-100236
Patent Document 4: WO 03/084991 A1
Non-Patent Document 1: Grant-in-Aid for Scientific Research from The Ministry of Health, Labours and Welfare of Japan on 2002, Annual Report of Research Project for Prevention, Treatment, etc. of Immunological Allergic Diseases (Vol. 1, pp. 101 to 103, issued on March 2003 by The Japanese Ministry of Health, Labour and Welfare)

DISCLOSURE OF THE INVENTION

A method of administering an inhibitor of production of an IgE antibody against an antigen shows an effect to a certain degree, however, it does not essentially block the pathogen, and therefore, although it is useful in alleviating symptoms, it is not an essential treatment. In addition, since the origins of pathogens have been sought only from food or foreign substances present in the environment, no attention was paid to substances produced in the body.

The invention of this application has been made in view of the circumstances as described above, and its object is to provide an atopic dermatitis inducer produced by a patient of his or her own as a causative factor of atopic dermatitis.

Further, an object of the invention is to provide an antibody binding to the above-mentioned inducer.

Still further, an object of the invention is to provide a method of diagnosing atopic dermatitis using the above-mentioned inducer and/or antibody.

Still further, an object of the invention is to provide a drug for desensitization therapy of atopic dermatitis containing the inducer as an active ingredient.

This application provides the following inventions as an invention for solving the above-mentioned problems.

(1) An atopic dermatitis inducer activating mast cells and basophils upon binding to a human own IgE antibody, which includes a purified human secretion fraction, or an antigenic molecule or an antigenic determinant in the purified fraction, and is obtained through the following steps of:

filtering a human secretion, removing insoluble matters and collecting the filtrate;

mixing the filtrate with a ConA-affinity carrier and collecting the supernatant; and separating a component having a histamine-releasing activity from the supernatant by column chromatography.

(2) The atopic dermatitis inducer of said the invention (1), wherein the column chromatography is anion exchange column chromatography and/or reverse phase column chromatography.

(3) An antibody prepared by using the atopic dermatitis inducer of said invention (1) as an antigen, and specifically binding to the atopic dermatitis inducer of said invention (1).

(4) A method of diagnosing atopic dermatitis, which comprises testing whether or not an IgE antibody binding to the atopic dermatitis inducer of said invention (1) or (2) exists in the serum of a subject and determining that the subject whose serum contains the IgE antibody is a patient with atopic dermatitis or a high-risk individual for atopic dermatitis.

(5) A method of diagnosing atopic dermatitis, which comprises adding the atopic dermatitis inducer of said invention (1) or (2) to a leukocyte fraction collected from the blood of a subject, and determining that the subject is a patient with atopic dermatitis or a high-risk individual for atopic dermatitis from the degree of histamine release in the leukocyte fraction.

(6) A method of diagnosing atopic dermatitis, which comprises testing whether or not a substance binding to an antibody of said invention (3) exists in a biological sample of a subject, and determining that the subject whose sample contains the substance is a patient with atopic dermatitis or a high-risk individual for atopic dermatitis.

(7) A reagent for determining a high-risk individual for atopic dermatitis, which comprises a patch test material having the atopic dermatitis inducer of said invention (1) or (2).

(8) A drug for desensitization therapy of atopic dermatitis, which contains the atopic dermatitis inducer of said invention (1) or (2) as an active ingredient.

That is, the "atopic dermatitis inducer" of this invention includes a "purified human secretion fraction" (a fraction not adsorbed to a cationic column, which is not adsorbed to a cationic exchange resin or a ConA column) of its own, or an "antigen molecule" or an "antigen determinant" contained in the purified fraction. Examples of the one that can become an antigen molecule include constituent molecules of the living body such as proteins, carbohydrates, lipids, complexes or modifications thereof and the like, however, other synthetic compounds, non-natural compounds and the like can become an antigen. In general, what an antibody recognizes is not the entire antigen molecule, but a specific site on its surface. This specific site or structure is called an antigen determinant (epitope). The site (epitope) that an antibody recognizes includes not only a primary structure such as an amino acid sequence of protein, but also a specific tertiary structure constituted by plural portions on the molecule and the like. Accordingly, a high-molecular weight molecule has plural antigen determinants on its surface in many cases.

The term "human secretion" means secretion from the inside of the human body or from the secretory glands of the body surface, and particularly means saliva, tear, milk and sweat respectively secreted from exocrine glands (salivary glands, tear glands, mammary glands and sweat glands). Incidentally, "purified human secretion fraction" is sometimes referred to as "Fr.D" in the following description.

As described above, the inventors have already reported on an antigen contained in sweat and an atopic dermatitis inducing protein (Non-Patent Document 1 and Patent Document 4). The main component of a sweat antigen described in Non-Patent Document 1 is adsorbed to a cationic exchange resin. In addition, the atopic dermatitis inducing protein in Patent Document 4 is contained in a fraction adsorbed to a cationic exchange resin and a ConA column (fraction adsorbed to a cationic column), and the substances in Non-Patent Document 1 and Patent Document 4 are practically the same. On the contrary, Fr.D according to this invention is a fraction not adsorbed to a cationic column, which is not adsorbed to a cationic exchange resin or a ConA column.

Further, Fr.D (fraction not adsorbed to a cationic column) according to this invention is different from the fraction adsorbed to a cationic column (Non-Patent Document 1 and Patent Document 4) in terms of the effect as described below.

i: When the clinical results for the non-adsorbed fraction (Fr.D) and the adsorbed fraction were compared, in the Fr.D group, 36 out of 40 patients with atopic dermatitis (90.0%) were determined to be positive (Example 5), while in the adsorbed fraction group, only 26 out of 36 patients (72.2%) showed positive (Non-Patent Document 1, page 101, left column, line 41).

ii: When a histamine-releasing activity on blood cells of AD patients was measured by using Fr.D purified from sweat and a fraction obtained from the same sweat by the method shown in Patent Document 4, the histamine-releasing activity of the former was 45.5% at a concentration of 7.74 µg/ml, while that of the latter was 5.1% at a concentration of 100 µg/ml. This shows that the former has an extremely high activity compared with the latter.

The other terms and concepts in this invention will be defined in detail in the description of the embodiments or Examples of the invention. In addition, various techniques used for implementing this invention can be easily and surely carried out by those skilled in the art based on known literatures and the like except for the techniques whose sources are particularly specified. For example, preparation of a therapeutic drug of this invention is described in Remington's Pharmaceutical Sciences, 18th Edition, ed. A. Gennaro, Mack Publishing Co., Easton, Pa., 1990, and techniques of genetic engineering and molecular biology are described in Sambrook and Maniatis, in Molecular Cloning; A Laboratory Manual, Cold Spring Harbor Laboratory Press, New York, 1989; Ausubel, F. M. et al., Current Protocols in Molecular Biology, John Wiley & Sons, New York, N.Y., 1995 and the like.

BEST MODE FOR CARRYING OUT THE INVENTION

An atopic dermatitis inducer of the invention (1) is a substance which is contained in a human secretion, binds to a human own IgE antibody and activates mast cells and basophils, and is a purified fraction purified through the following method, an antigen molecule or an antigen determinant contained in the purified fraction.
(I) A step of filtering a human secretion, removing insoluble matters and collecting the filtrate.

For example, insoluble matters (precipitate) are removed by passing a human secretion (saliva, tear or sweat) through a filter. The pore size of the filter can be appropriately selected from about 0.10 to 1.00 μm depending on the type of the secretion or the like. For example, in the case of filtering sweat, it is preferred to use a filter with a pore size of 0.15 to 0.30 μm (Bottle Top Filter 431174, Corning) or the like.
(II) A step of mixing the filtrate with a ConA-affinity carrier and collecting the supernatant.

As the ConA-affinity carrier, a commercially available product (e.g., ConA-Sepharose, Amersham Parmacia, glycoprotein adsorption capacity: 45 mg/ml; ConA-agarose, Calbiochem, glycoprotein adsorption capacity: 3.5 mg/ml; ConA-agarose, Sigma, glycoprotein adsorption capacity: 3 to 6 mg/ml and the like) can be used. A required amount of the affinity carrier should be an amount sufficient to adsorb the total amount of glycoprotein in the filtrate, and adsorption treatment is carried out by mixing and stirring the mixture at around 4° C. to room temperature for several hours to overnight. After the treatment, the supernatant (a fraction not adsorbed to the ConA-affinity carrier) is collected by centrifugation, filtration or the like.
(III) A step of separating a component having a histamine-releasing activity from the supernatant by column chromatography.

A known column chromatography technique (e.g., ion exchange chromatography, reverse phase chromatography, size exclusion chromatography, partition chromatography, affinity chromatography, slalom chromatography and the like) can be used, however, preferably anion exchange chromatography or reverse phase chromatography is used. In addition, in the case when both are used, it is preferred to perform anion exchange chromatography and then perform reverse phase chromatography (invention (2)).

As the anion exchange chromatography, a commercially available anion exchange column such as MonoQ HR 10/10 (Pharmacia Biotech) or UNO Q12 (BioRad) can be used. As for these columns, one equilibrated with a buffer (e.g., 20 mM Tris-HCl (pH 8.0) or the like) in advance is used. As the reverse phase chromatography, a commercially available reverse phase column such as SOURCE 15RPC ST 4.6/100 (Pharmacia Biotech) can be used. In the case where a fraction obtained by anion exchange chromatography is loaded onto a reverse phase chromatography column, the previous fraction is diluted to around 5- to 20-fold with distilled water or the like, and loaded onto the subsequent chromatography column.

In addition, the histamine-releasing activity can be evaluated by measuring the amount of histamine by a known method described in the report (Koro, O. et al., J. Allergy Clin. Immunol. 103, 663-670, 1999).

By the steps described above, a purified human secretion fraction (Fr.D) as an atopic dermatitis inducer can be obtained.

Figure 2:
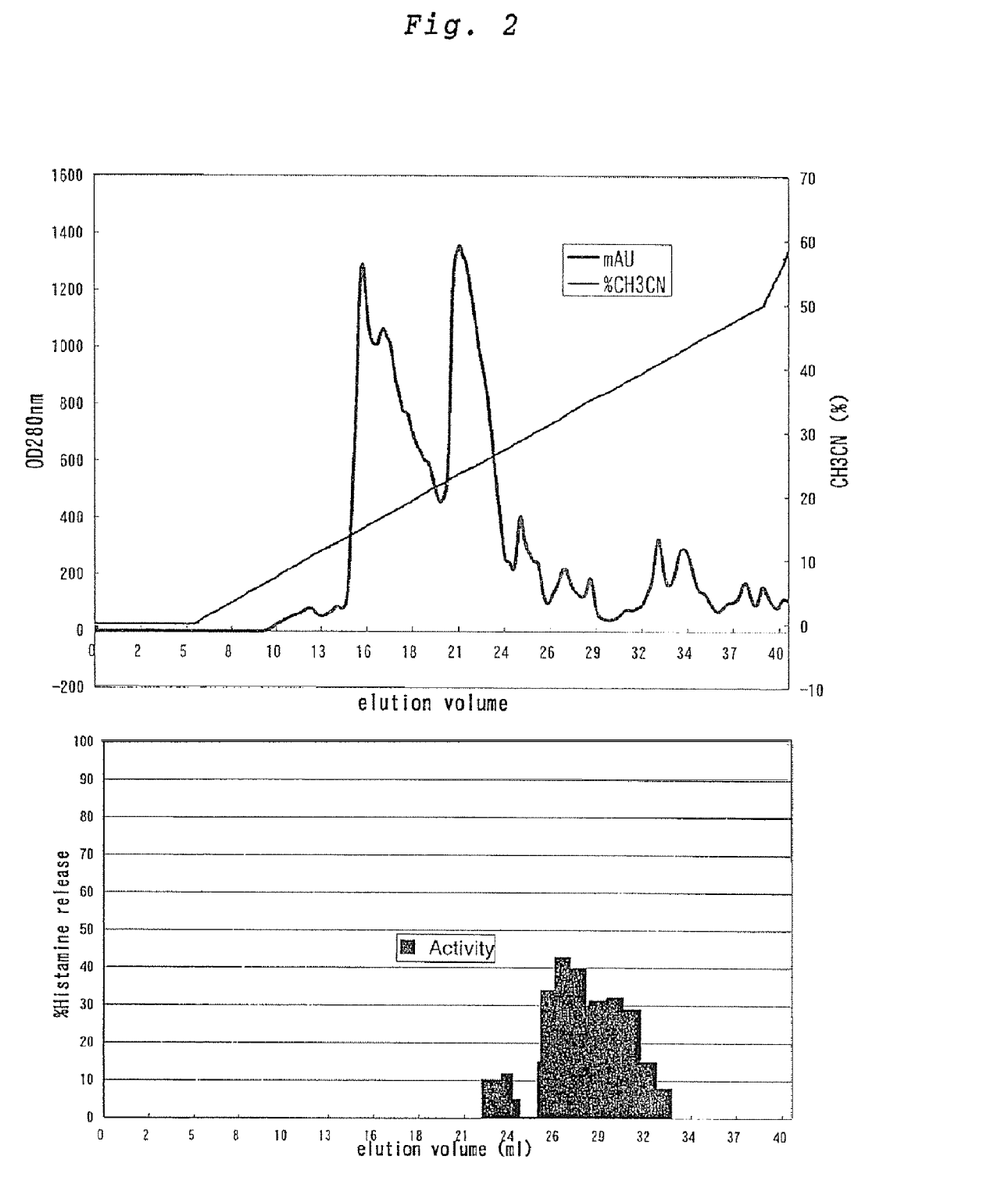
FIG. 2 shows the separation results using a reverse phase column. The upper graph shows an elution pattern of a fraction with an activity purified with an anionic column using a reverse phase column, and the lower graph shows the histamine-releasing activities of the respective fractions.
Figure 3:
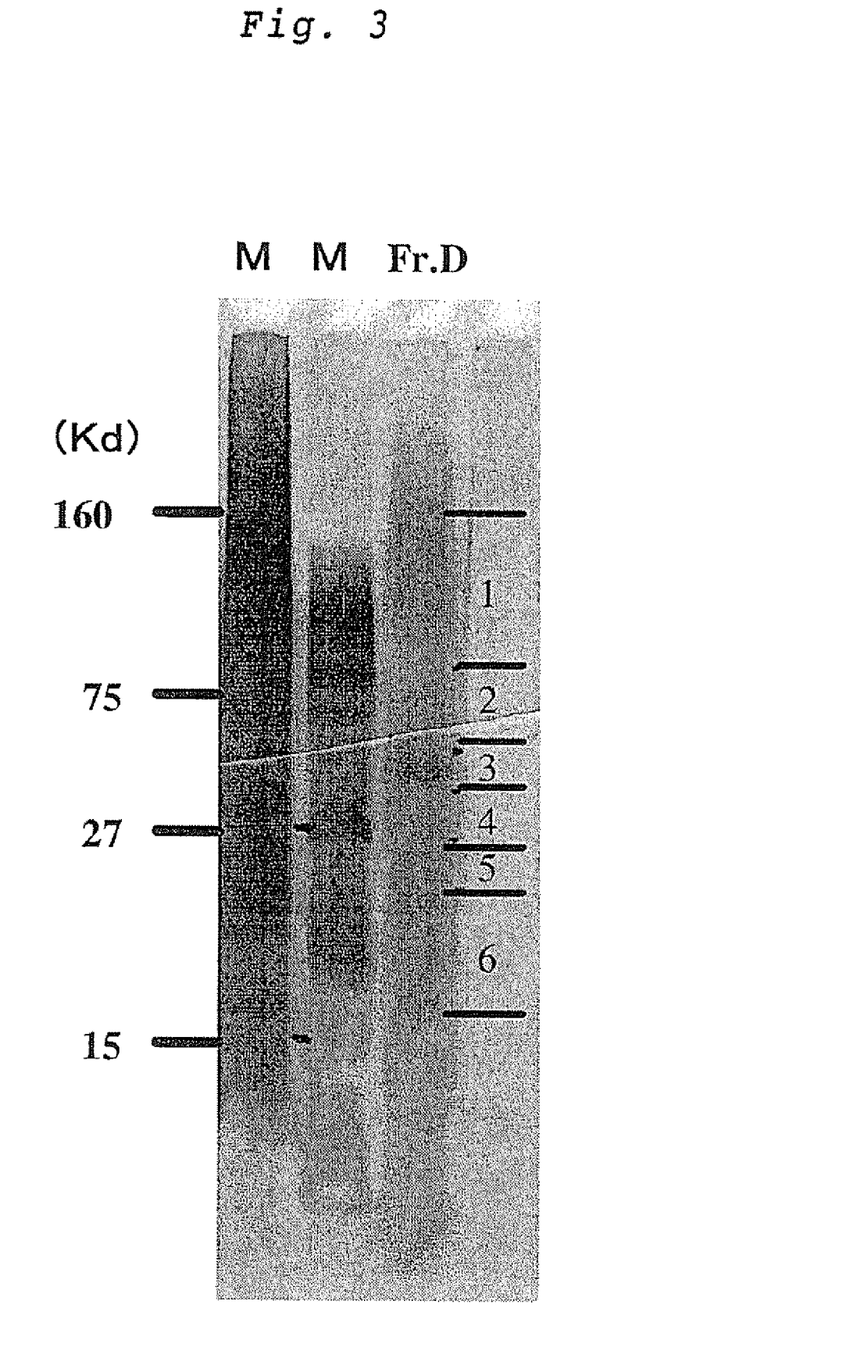
FIG. 3 shows the development pattern of Fr.D by a 15% polyacrylamide gel electrophoresis.
Figure 4:
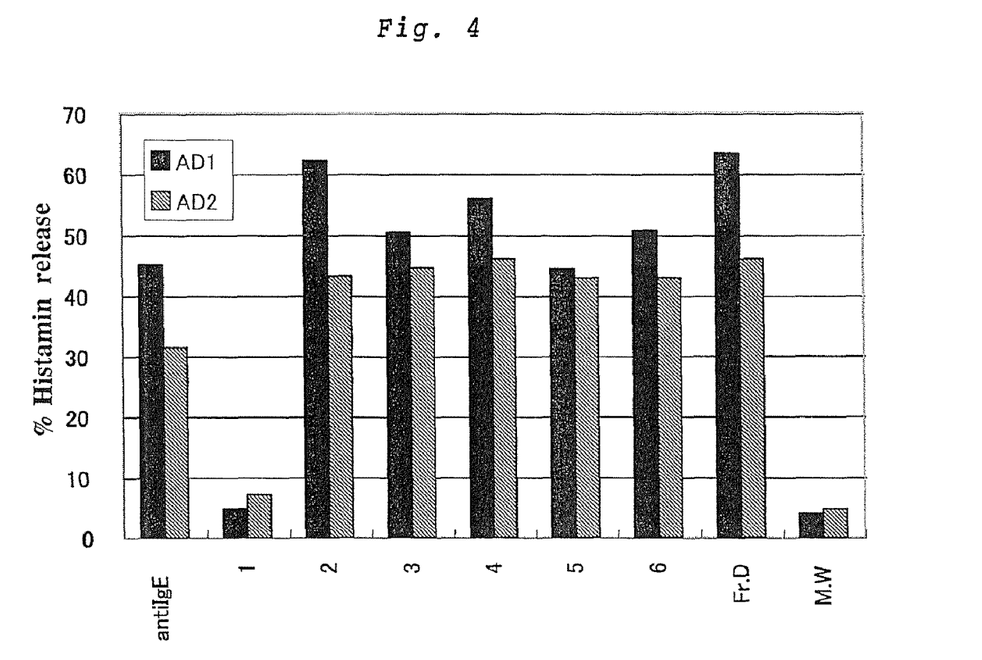
FIG. 4 shows the histamine-releasing activity of a fraction eluted from a native PAGE using blood cell fractions of 2 patients with atopic dermatitis (AD1 and AD2). The number corresponds to the fraction number in FIG. 3. "antiIgE" indicates an anti-IgE antibody and "MW" indicates a molecular weight marker protein used as a negative control.

That is, as shown in the following Examples, when fractionation was carried out with an anion exchange column using a histamine-releasing activity as an indicator, the inducer contained in Fr.D was eluted at a NaCl concentration of 0.05 M to 0.34 M (FIG. 1), when fractionation was carried out with a reverse phase column, it was eluted at an acetonitrile concentration of 25% to 40% (FIG. 2); and when development was carried out with a native PAGE (polyacrylamide gel electrophoresis), it was observed as a rather broad band though it had dark and light staining (FIG. 3). Further, it was confirmed that the region ranging from band 2 to band 6 shown in FIG. 3 has a histamine-releasing activity (FIG. 4). This shows that a number of inducers are contained in Fr.D.

Figure 5:
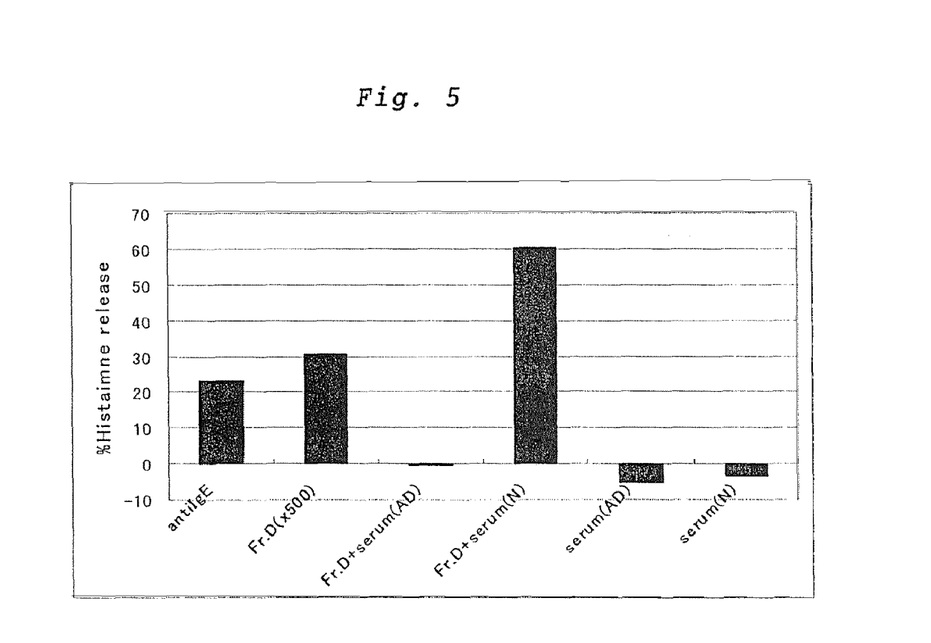
FIG. 5 shows the results of a test of absorbing Fr.D activity by the serum of a patient with atopic dermatitis, and shows a histamine-releasing activity when the serum of a patient with atopic dermatitis or a normal subject was mixed with Fr.D. "antiIgE" indicates an anti-IgE antibody, "Fr.D (×500)" indicates a 500-fold dilution of Fr.D, "serum (AD)" indicates the serum of a patient with atopic dermatitis, and "serum (N)" indicates the serum of a normal subject.

In addition, when the serum of a patient with atopic dermatitis is added to Fr. D in advance, the histamine-releasing activity of Fr. D is lost (FIG. 5). Further, when the serum of a patient is added at 37° C. for 90 minutes to blood cells of a normal subject treated with lactic acid, and then the cells are washed, the cells acquire the reactivity to Fr.D. Therefore, when Fr.D is added, the cells will come to release histamine. Since such a change does not occur when the serum of a normal subject is added, these results show that an atopic dermatitis inducer contained in Fr. D activates mast cells and basophils via a substance specifically contained in the serum of a patient with atopic dermatitis. Further, imparting of Fr.D responsiveness to the blood cells of a normal subject by the serum of a patient with atopic dermatitis is completely inhibited by adding non-specific IgE derived from the serum of a patient with myeloma in advance to the blood cells of a normal subject treated with lactic acid or by heating the serum of a patient with atopic dermatitis at 56° C. for 1 hour. This shows that a transmitter contained in the serum of a patient with atopic dermatitis is specific IgE (Example 6).

Further, when sensitization was carried out with IgE purified from a patient with atopic dermatitis, degranulation occurred in a concentration dependent manner by a purified sweat antigen (Fr.D) (Example 7). This shows that the specific IgE can be detected by using the sweat antigen and that diagnosis of atopic dermatitis is possible by using the serum of a patient.

Fr.D is stable in heating at 85° C. for 15 minutes. In addition, though it shows resistance to DNase and lipase, when Fr.D is treated with a protease, it lose the histamine-releasing activity, accordingly, the inducer has at least a protein or a peptide as one of its constituents.

The above description indicates the possibility that the above-mentioned protein or peptide or a substance forming a complex of the above-mentioned protein or peptide has been subjected to diverse modifications such as modification with sugar chains.

In addition, when the inducer collected from band 1 to band 5 in the denatured PAGE (FIG. 6) was analyzed with a mass spectrometer, peptide fragments having amino acid sequences LGKDAVEDLESVGK (SEQ ID NO:1) and DAVEDLESVGK (SEQ ID NO:2) were obtained from any of the bands. These sequences correspond to amino acid number 83 to 96 and 86 to 96 of known Dermcidin (Br. J. Cancer, 276, 5707-5713, 2000; hereinafter referred to as "DCD"), therefore, at least one of the proteins or the peptides constituting the inducer is DCD or a fragment thereof. A peptide at the C-terminal side of DCD (DCD1) has been reported as an antibacterial peptide secreted from a sweat gland (Nature Immunology, 2, 1133-1137, 2001), however, it has been totally unknown that DCD and DCD1 are inducing proteins causing atopic dermatitis by binding to an IgE antibody of the person secreting them and activating mast cells and basophiles.

DCD or a partial peptide thereof can be isolated and purified from human sweat by the same method as in Example 1 described later. In addition, it can also be synthesized chemically based on a known method of peptide synthesis (Shin Seikagaku Jikken Koza 1, Protein IV, Synthesis and Expression, Tokyo Kagaku Dojin, 1992) or the like. Further, it can also be prepared by a method of preparing a protein or a peptide with an in vitro transcription/translation system using a DNA sequence (GenBank No. NM_053283) encoding the protein or by a known genetic engineering technique using an appropriate host-vector system (a prokaryotic cell such as *Bacillus subtilis* or a eukaryotic cell such as yeast, an insect cell or a cell of an animal or a plant) (e.g., Shin Seikagaku Jikken Koza 1, Protein IV, Synthesis and Expression, Tokyo Kagaku Dojin, 1992; Shin Seikagaku Jikken Koza 2, Nucleic Acids III, Recombinant DNA Techniques, edited by Japanese Biochemical Society, 1992; Molecular Biology Protocols, The 2nd revised edition, edited by Koike K, Sekiya T and Kondo H., Nankodo, 1999).

The inducer of the invention (1) binds to 2 or more antibodies and exerts its physiological activity by allowing it to have 2 or more antigen determinants. Accordingly, the atopic dermatitis inducer of this invention can be an inducer containing 2 or more antigen determinants. Since such an antigen determinant has the same physiological activity (i.e., atopic dermatitis inducing activity) as the inducer, it can be used in a diagnostic Method or as an active ingredient of a drug for desensitization therapy of this invention. In addition, the antigen determinant of this invention may be one. Such an antigen determinant can be used as an antigen for antibody production, a material for the diagnostic method of the invention (4), or a material for desensitization therapy.

Further, the antigen determinant can be used after allowing it to bind to a synthetic polymer or the like such as a protein (e.g., BSA), a polysaccharide or polyacrylamide.

The invention (3) is an antibody characterized by being prepared by using an atopic dermatitis inducer of the above-mentioned invention (1) as an antigen and specifically binding to the atopic dermatitis inducer of the above-mentioned invention (1).

The antibody is a polyclonal antibody or a monoclonal antibody, and a whole molecule that can bind to the above-mentioned inducer or its epitope site, and Fab, F(ab')2 and Fv fragments and the like are all included. Such an antibody can be prepared in accordance with a known method described in a document (Shin Seikagaku Jikken Koza 12, Molecular Immunology III, Antigens, Antibodies and Complements, Tokyo Kagaku Dojin, 1992; "Monoclonal Antibody", co-authored by Nagamune H. and Terada H., Hirokawa Shoten, 1990; "Monoclonal Antibodies", James W. Goding, third edition, Academic Press, 1996 or the like).

In addition, in the antibody of this invention (3), an antibody labeled with a labeling substance is also included. As the labeling substance, an enzyme, a radioisotope or a fluorescent dye can be used. There is no particular limitation on the enzyme as long as it fulfills the requirements such that its turnover number is large, it is stable even upon binding to an antibody and it can specifically stain a substrate, and an enzyme to be used in common EIA such as peroxidase, β-galactosidase, alkaline phosphatase, glucose oxidase, acetylcholine esterase, glucose-6-phosphate dehydrogenase, malate dehydrogenase or the like can also be used. In addition, an enzyme inhibitor, a coenzyme or the like can also be used. The conjugation of such an enzyme with the antibody can be carried out by a known method using a crosslinking agent such as a maleimide compound. As the substrate, a known substance can be used according to the type of an enzyme to be used. For example, in the case where peroxidase is used as the enzyme, 3,3',5,5'-tetramethylbenzidine can be used, and in the case where alkaline phosphatase is used as the enzyme, p-nitrophenol or the like can be used. As the radioisotope, those used in a common RIA such as 125I or 3H can be used. As the fluorescent dye, those used in a common fluorescence antibody technique such as fluorescein isothiocyanate (FITC) or tetramethylrhodamine isothiocyanate (TRITC) can be used.

In the method of diagnosing atopic dermatitis of the invention (4), a test is performed on whether or not an antibody binding to the above-mentioned atopic dermatitis inducer is present in the serum of a test subject and the test subject whose serum contains the antibody is determined to be a patient with atopic dermatitis or a high-risk individual for atopic dermatitis.

In a specific diagnosis, for example, the serum of a test subject is brought into contact with the atopic dermatitis inducer to react the inducer with the IgE antibody in the serum of the test subject in a liquid phase.

Further, a labeled IgE antibody specifically binding to the IgE antibody in the serum is reacted, and the signal of the labeled IgE antibody may be detected. As the labeling substance for the labeled IgE antibody, an enzyme, a radioisotope or a fluorescent dye as illustrated in the above-mentioned labeled antibody can be used. In the case of using an enzyme, a substrate which develops color by being decomposed due to an enzymatic action is added, the activity of the enzyme is obtained by optically measuring the amount of the decomposed substrate, the obtained activity is converted into the amount of bound antibody, and the amount of the antibody is calculated in comparison with the standard value. In the case of using a radioisotope, the amount of radiation emitted by the radioisotope is measured with a scintillation counter or the like. In addition, in the case of using a fluorescent dye, the fluorescent amount may be measured with a measuring apparatus combined with a fluorescence microscope.

As the detection of the signal, for example, Western blot analysis can be adopted. Alternatively, the conjugate of the antigen peptide, the antibody in the serum and the labeled IgE antibody is separated by a known separation method (a chromatography, a salting out method, an alcohol precipitation method, an enzyme method, a solid phase method or the like), and the signal of the labeled IgG antibody may be detected.

The diagnostic method of the invention (4) can also be carried out as a method in which the inducer is immobilized on a plate or a membrane, and the binding to the antibody in the serum of a test subject is tested on this substrate. By immobilizing the inducer on a substrate, un-bound labeled binding molecule can be easily removed.

The method of this invention (4) permits the determination how much the antibody to be detected is present as well as the diagnosis of atopic dermatitis. A standard (standard curve or the like) is constructed in advance, and the amount of the antibody obtained from the serum of a test subject is compared with the standard, whereby the accurate amount of the antibody can be measured, and it becomes possible to assess the degree of the disease or the degree of the risk of occurrence of the disease with a high accuracy.

The invention (5) is a method of diagnosing a patient with atopic dermatitis or a high-risk patient for atopic dermatitis from the amount of histamine released by adding the above-mentioned inducer to a leukocyte fraction. The amount of histamine may be measured by a method described in the document (Koro, O. et al., J. Allergy Clin. Immunol. 103, 663-670, 1999).

Sabroe et al. have set the cut-off value for determination to be 5% from the study of the amount of released histamine in a patient with urticaria (the ratio of the amount of secreted histamine to the total amount of histamine) (J. Am. Acad. Dermatol., 40, 443-450, 1999). Therefore, when the amount of histamine released by Fr.D was measured for leukocyte fractions derived from a normal subject and a patient with atopic dermatitis by using a cut-off value of 5%, 3 out of 33 normal subjects (9.1%) and 36 out of 40 patients with atopic dermatitis (90%) were determined to be positive (Example 5).

In the diagnostic method of the invention (6) of this application, a test is performed on whether or not an inducer binding to the antibody of the above-mentioned invention (3) is present in a biological sample (a secretion such as saliva, sweat or tear) of a test subject and determining that the test subject whose sample contains the inducer is a patient with atopic dermatitis or a high-risk individual for atopic dermatitis.

One embodiment of the diagnostic method of this invention (6) is a method in which binding of an antibody to an inducer is performed in a liquid phase system. For example, a labeled antibody is brought into contact with a biological sample to bind the labeled antibody to an inducer, and this conjugate is separated in the same manner as in the above-mentioned invention (4) and the labeled signal is detected in the same manner.

In another diagnostic method in the liquid phase system, an antibody (primary antibody) is brought into contact with a biological sample to bind the primary antibody to an inducer, a labeled antibody (secondary antibody) is bound to this conjugate, and the labeled signal in the conjugate of the third party is detected. In addition, in order to further enhance the signal, first a non-labeled secondary antibody is bound to the conjugate of an antibody and an inducer, and a labeling substance may be bound to this secondary antibody. Such conjugation of the labeling substance to the secondary antibody can be carried out by, for example, biotinylating the secondary antibody and avidinylating the labeling substance. Alternately, an antibody (tertiary antibody) that recognizes a partial region of the secondary antibody (e.g., Fc region) is labeled, and the tertiary antibody may be bound to the secondary antibody. Note that with regard to the primary antibody and the secondary antibody, monoclonal antibodies can be used for both antibodies, or a polyclonal antibody can be used for either of them. The separation of the conjugate from the liquid phase or the detection of the signal can be carried out in the same manner as in the above-mentioned invention (4).

Another embodiment of the diagnostic method of the invention (6) is a method in which the binding of an antibody to an inducer is tested in a solid phase system. This method in the solid phase system is a preferred method because of the detection of a very little amount of the inducer and the convenience of the operation. More specifically, this method in the solid phase system is a method in which an antibody (primary antibody) is immobilized on a resin plate, membrane or the like, an inducer is bound to this immobilized antibody, a non-bound molecule is washed out, a labeled antibody (secondary antibody) is bound to the conjugate of the antibody and the inducer remaining on the plate, then the signal of this secondary antibody is detected. This method is what is called a "sandwich method", and in the case of using an enzyme as a marker, it is a widely used method as "ELISA (enzyme linked immunosorbent assay)". With regard to the primary antibody and the secondary antibody, monoclonal antibodies can be used for both antibodies, or a polyclonal antibody can be used for either of them. The detection of the signal can be carried out in the same manner as in the above-mentioned invention (6). In addition, by using an ELISA kit, it is possible to carry out such a diagnostic method conveniently and extensively.

The method of this invention (6) permits the determination how much the atopic dermatitis inducer is present as well as the diagnosis of atopic dermatitis. A standard (standard curve or the like) is constructed in advance, and the amount of the protein obtained from the biological sample of a test subject is compared with the standard, whereby the accurate amount of the protein can be measured, and it becomes possible to assess the degree of the disease or the degree of the risk of occurrence of the disease with a high accuracy.

Implementation of the above-mentioned invention (4) or (6) can be appropriately performed according to a document (The 4th revised edition, Watanabe Nakane Enzyme Immuno Assay, edited by Nagura H., Osamura Y., Tsutsumi H., Gakusai Kikaku, 2002, or the like) other than the above-mentioned examples.

In addition, the diagnosis of atopic dermatitis can be carried out by what is called a "patch test" using the inducer of the above-mentioned invention (1). The patch test is carried out widely in the dermatology field as a convenient test method for contact allergy. When contact allergy is present, not only the area of dermatitis but also the skin throughout the body is sensitized, therefore, the cause of the contact dermatitis can be determined by artificially reproducing allergic contact dermatitis on the healthy skin. More specifically, the above-mentioned inducer is dropped or coated onto an adhesive patch and placed on the upper back, upper arm, thigh or the like. Determination is carried out according to the ICDRG (International Contact Dermatitis Research Group) standard after 2 days, 3 days and 1 week. The condition where there is no skin reaction is determined to be (−), the condition where the area exposed to the agent on the patch has erythema and edema is determined to be (+) (++) or (+++) depending on the degree of the reaction. This application provides a determination reagent of the invention (7) as a means that can diagnose atopic dermatitis by such a patch test conveniently, uniformly and extensively at low cost.

The invention (8) is a drug for desensitization therapy of atopic dermatitis characterized by containing the above-mentioned atopic dermatitis inducer as an active ingredient.

"Desensitization therapy" is a therapeutic method in which as for an allergy associated with an IgE antibody, a small amount of therapeutic allergen is administered and the dose is gradually increased at intervals of predetermined number of days, so that even if a causative allergen invades the body, an allergic reaction does not occur. Since the atopic dermatitis inducer of this invention has an atopic dermatitis inducing activity as described above, it can be a therapeutic allergen for desensitization.

As shown in Example 9, when desensitization therapy using Fr.D was attempted in patients with atopic dermatitis who actually show an allergic reaction to sweat, improvement was observed in the intradermal test and in the clinical findings.

This drug for desensitization therapy can be formulated by uniformly mixing the above-mentioned inducer with a pharmacologically acceptable carrier. The carrier can be appropriately selected from a wide range depending on the dosage form of the drug, however, it is preferred that the drug of this invention is in a unit dosage form that can be administered orally or by injection.

An oral liquid preparation such as a suspension or a syrup can be prepared by using water, a saccharide such as sucrose, sorbitol or fructose, a glycol such as polyethylene glycol, an oil such as sesame oil or soybean oil, a preservative such as alkyl p-hydroxybenzoate, a flavor such as strawberry flavor or peppermint, or the like.

A powder, a pill, a capsule and a tablet can be formulated by using a excipient such as lactose, glucose, sucrose or mannitol, a disintegrator such as potato starch or sodium alginate, a lubricant such as magnesium stearate or talc, a binder such as polyvinyl alcohol, hydroxypropyl cellulose or gelatin, a surface active agent such as a fatty acid ester, a plasticizer such as glycerin or the like. A tablet and a capsule is a preferred unit dosage form in the preparation of this invention in terms of easiness of administration. When a tablet or a capsule is prepared, a solid pharmaceutical carrier is used.

A solution for injection can be formulated by using a salt solution, a glucose solution or a mixture of a salt solution and a glucose solution, a carrier comprising a variety of buffers or the like. In addition, it is formulated into a powder and an injectable solution may be prepared by mixing the powder with the above-mentioned liquid carrier at the time of use.

The administration schedule for the drug for desensitization therapy of this invention varies depending on the patient's age and body weight, and the symptoms, the administration route and the like. However, with regard to the amount of protein or peptide as a therapeutic allergen, it is preferred that a intradermal test is carried out in advance, a threshold is determined on an individual basis and the first dose is set to the amount around the threshold. The dosing interval after the first dose and the increasing level of the allergen can be appropriately determined depending on the degree or the presence of allergic reaction. Eventually, the allergen in an amount around 10,000-fold threshold can be administered. Therefore, for example, when the drug for desensitization therapy of this invention is formulated such that the first dose of allergen is set at 1 ng/ml×0.05 ml, the drug for the final administration can be formulated at a dose of 10 mg/ml×0.05 ml.

EXAMPLES

Hereunder, the invention of this application will be described in more detail and specifically with reference to Examples, however, the invention of this application is not limited to the following examples.

Example 1

Purification of Fraction Having Histamine-Releasing Activity (Fr.D)

1-1. Step of Filtering Human Sweat, Removing Insoluble Matters and Collecting the Filtrate 500 ml of human sweat was filtered (0.22 μm), and the precipitate was removed. A filtrate with a total protein amount of 1.07 mg roughly estimated from the optical density (OD, 280 nm) was obtained.

1-2. Step of Mixing the Filtrate with a ConA-affinity Carrier and Collecting the Supernatant To the sweat subjected to filtering, 24 ml of a ConA-affinity carrier (ConA-Sepharose, Amersham Pharmacia; glycoprotein adsorption capacity: 45 mg/ml) was added, and stirring was carried out overnight at 4° C., and then the supernatant (a fraction not adsorbed to ConA-Sepharose) was collected.

Figure 1:
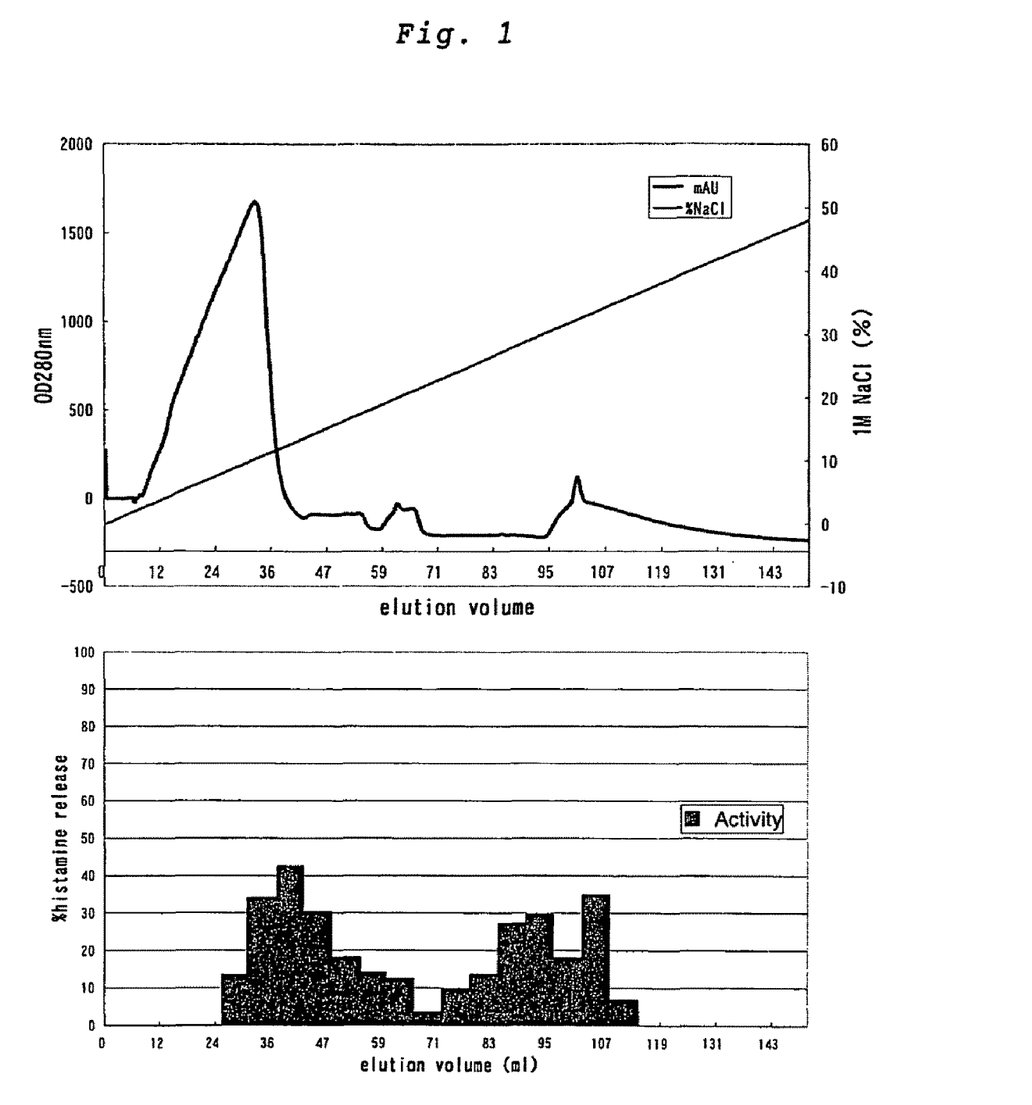
FIG. 1 shows the separation results using an anionic exchange column. The upper graph shows an elution pattern of a fraction not adsorbed to ConA Sepharose using an anionic column, and the lower graph shows the histamine-releasing activities of the respective fractions.

1-3. Step of Separating the Supernatant with an Anionic Exchange Column and Collecting a Fraction Having a Histamine-releasing Activity Onto an anionic exchange column (MonoQ HR 10/10; Pharmacia Biotech), which had been equilibrated 20 mM Tris-HCl (pH 8.0) in advance, the supernatant adjusted to pH 8.0 was loaded, and elution was carried out with a NaCl concentration gradient of 0 to 1 M. 2 μl of each of the eluted fractions and 48 μl of a leukocyte fraction were mixed and reaction was carried out at 37° C. for 40 minutes. Thereafter, the reaction mixture was centrifuged to separate a supernatant and a precipitate. Then, perchloric acid was added for denaturation, and the amount of histamine was measured by HPLC. The ratio of the amount of histamine in the supernatant to the total amount of histamine is defined as a histamine-releasing activity. As a result of the histamine release test, a fraction having an activity eluted at a NaCl concentration of 0.05 M to 0.34 M was collected (FIG. 1). The amount of histamine was measured according to the method described in the document (Koro, O. et al., J. Allergy Clin. Immunol. 103, 663-670, 1999).

1-4. Step of Separating the Above-mentioned Fraction Having an Activity with a Reverse Phase Column and Collecting a Fraction Having a Histamine-releasing Activity (Fr.D)

The collected fraction with the anionic column was diluted to 10-fold with 0.1% TFA in distilled water and loaded onto a reverse phase column (SOURCE 15RPC ST 4.6/100; Pharmacia Biotech), and elution was carried out with a concentration gradient from 0.1% TFA in distilled water to 0.1% TFA in CH3CN. After 2 μl of each of the eluted fractions was lyophilized to evaporate TFA or CH3CN, a histamine release test was carried out, and a fraction having a releasing activity (CH3CN with a concentration of 25% to 40%) was collected (FIG. 2).

A pattern when Fr.D was developed by a native 15% PAGE is shown in FIG. 3. As shown in FIG. 3, when the band was divided into 6 bands, and the histamine-releasing activity was measured for each band, the activity was observed from band 2 to band 6 (FIG. 4).

Example 2

Effect of Serum of Patient with Atopic Dermatitis on Histamine-releasing Activity of Fr.D Fr.D was collected, lyophilized, redissolved in PBS at a concentration of 1 mg/ml and used as an Fr.D standard. When 10 μl of a 50-fold dilution of the Fr.D standard was added to 40 μl of the serum of a patient with atopic dermatitis and preincubation was carried out at 37° C. for 30 minutes, the histamine-releasing activity was completely lost. On the contrary, when the serum of a normal subject was added, the histamine-releasing activity was not lost (FIG. 5). "antiIgE" and "Fr.D (×500)" are a positive control, and "serum (AD)" (serum of a patient) and "serum (N)" (serum of a normal subject) are a negative control.

Example 3

Enzyme Treatment 3-1. DNase Treatment and Lipase Treatment

To 5 μl of the Fr.D standard, DNase (Ambion) was added at a final concentration of 0.2 U/μl, or a pancreatic lipase (SIGMA) was added at a final concentration of 30 mU/μl, and incubation was carried out at 37° C. for 16 hours. In both cases, a decrease in the histamine-releasing activity was not observed.

3-2. Protease Treatment

To 5 μl of the Fr.D standard, 2 μg/μl of ProteinaseK (Ambion) or 2 μg/μl of Trypsin (SIGMA) was added to give a final concentration of 0.1 μg/μl, and incubation was carried out at 37° C. for 16 hours. In both cases, the histamine-releasing activity was completely lost.

Example 4

Determination of Amino Acid Sequence with Mass Spectrometer

Figure 6:
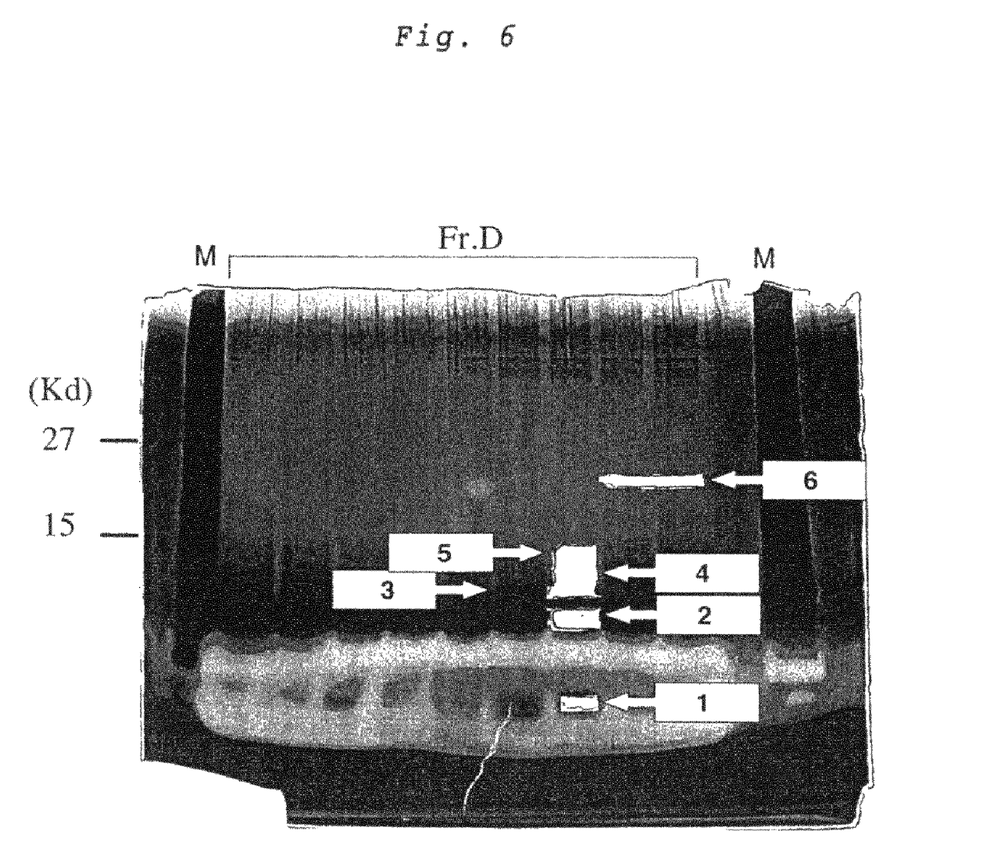
FIG. 6 shows the development pattern of Fr.D by a 15% denatured SDS-polyacrylamide gel electrophoresis. The bands shown in the drawing were excised from the gel and used for amino acid sequence determination.

A pattern when Fr.D was developed by a 15% SDS-PAGE is shown in FIG. 6 (the band number does not necessarily correspond to the number of FIG. 3). Each band was excised from the gel and subjected to in-gel trypsin digestion and inner amino acid sequence was determined by MS/MS measurement of the eluted fraction. As a result, in all the bands from band 1 to band 5, peptides having amino acid sequences of LGKDAVEDLESVGK (SEQ ID NO:1) and DAVEDLES-VGK (SEQ ID NO:2) were detected. From the database search, it was found that these sequences correspond to amino acid number 83 to 96 and 86 to 96 of Dermcidin.

The determination of the amino acid sequence with a mass spectrometer and the protein identification by database search were consigned to Prophoenix Co.

Example 5

Diagnosis of Patient with Atopic Dermatitis Using Fr.D

According to the methods described in Examples 1 and 2, the Fr.D standard was added (at a final concentration of 2 μg/ml) to a leukocyte fraction derived from a normal subject or a patient with atopic dermatitis, and the amount of released histamine was measured. When a cut-off value was set to be 5% based on the result and determination was carried out, 3 out of 33 normal subjects (9.1%) and 36 out of 40 patients with atopic dermatitis (90%) were determined to be positive.

Example 6

Detection of Sweat Antigen-specific IgE in Serum Using Human Peripheral Blood Basophils IgE was removed by lactic acid treatment from the surface of basophils in the peripheral blood of 3 normal subjects who do not have sensitivity to sweat, and these basophils were sensitized with IgE purified from the serum of a patient with atopic dermatitis and then stimulated by the purified sweat antigen Fr.D.

Figure 7:
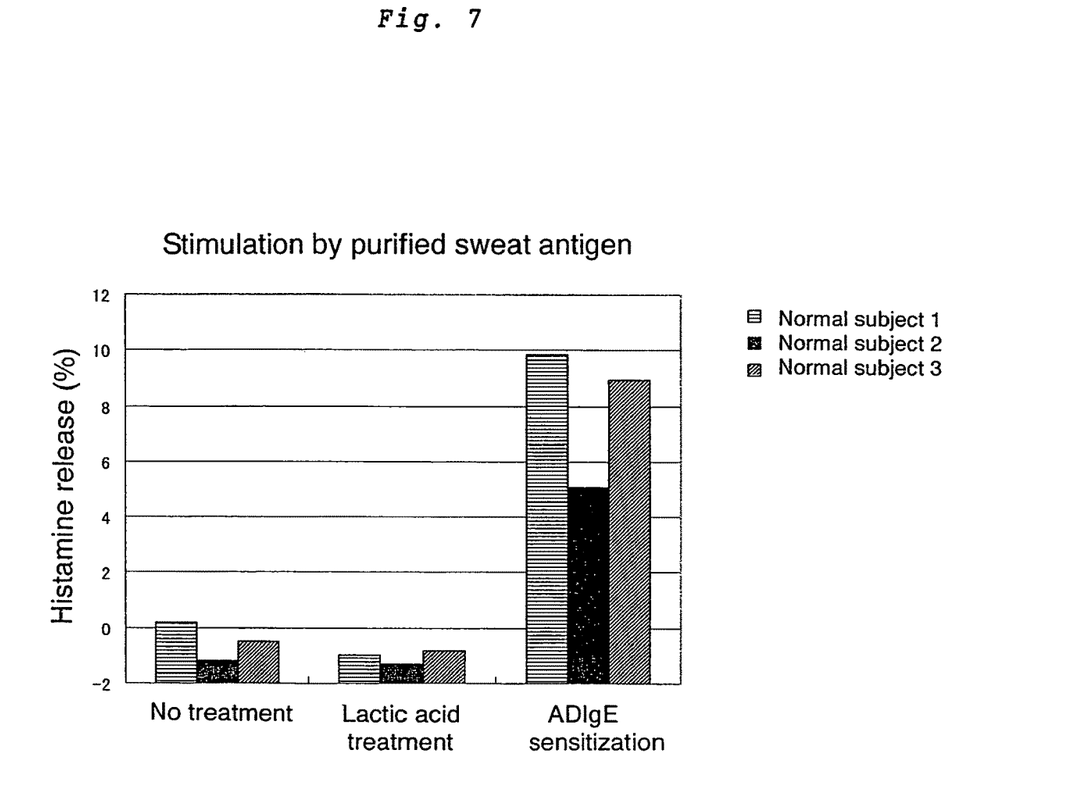
FIG. 7 shows the results of a histamine release test when a rat mast cell line was sensitized with purified IgE obtained from the serum of a patient with atopic dermatitis and stimulated by a purified sweat antigen (Fr.D). "RBL-2H3" indicates a rat mast cell line, "RBL-3D4" indicates a transformant cell line prepared by using RBL-2H3 as a host and introducing a human high affinity IgE receptor (FcεRI) α-subunit gene into the host, and "anti-IgE antibody" indicates an anti-human IgE antibody as a control.

As a result, no matter what the donor of the basophils was, histamine release was not observed by the sweat antigen stimulation after the lactic acid treatment. However, when these cells were sensitized with IgE purified from the serum of a patient with atopic dermatitis (ADIgE), histamine release by the sweat antigen stimulation was observed (FIG. 7). It could be confirmed that the presence of sweat antigen-specific IgE contained in the serum of a patient with atopic dermatitis can be detected from this test.

Example 7

Detection of Sweat Antigen-specific IgE in Serum Using Human Mast Cell Line

Figure 8:
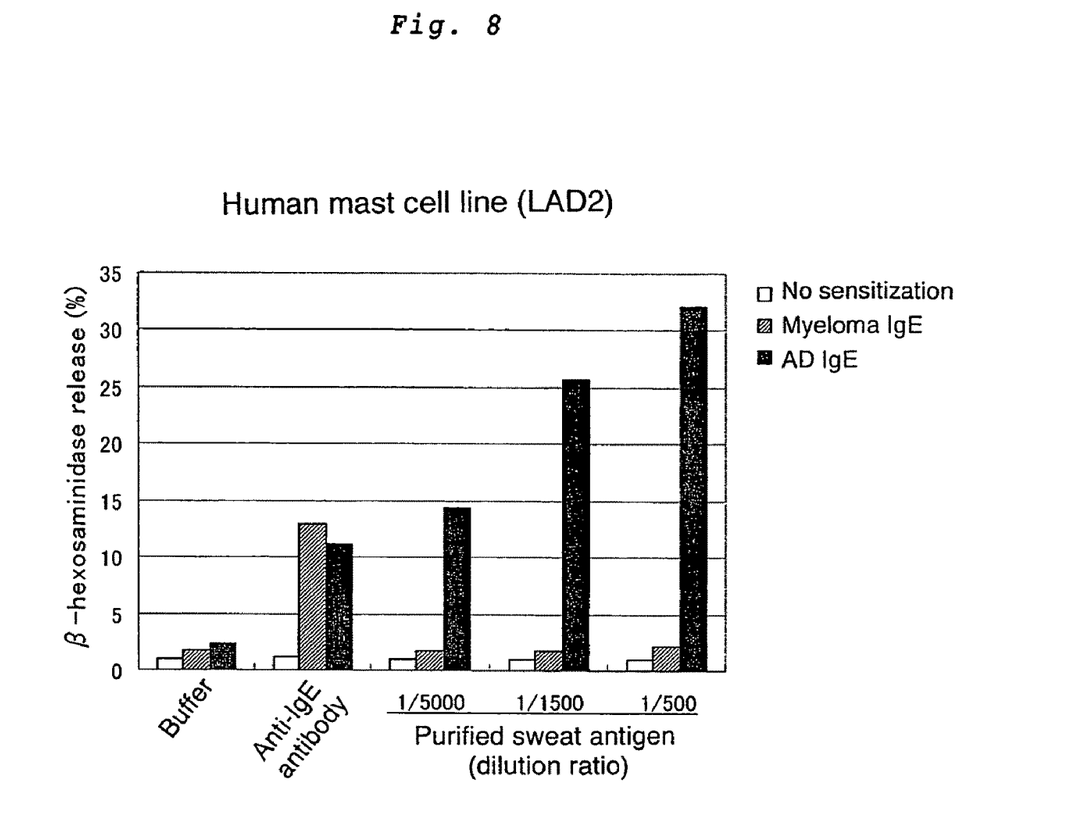
FIG. 8 shows the results of a histamine release test when basophils in the peripheral blood of a normal subject were treated with lactic acid and resensitized with IgE obtained from the serum of a patient with atopic dermatitis and then stimulated by a sweat antigen (Fr.D). "Not treated" indicates the case where basophils in the peripheral blood of a normal subject were stimulated by Fr.D, "Treated with lactic acid" indicates the case where basophils in the peripheral blood of a normal subject treated with lactic acid were stimulated by Fr.D, and "Sensitized with ADIgE" indicates the case where basophils in the peripheral blood of a normal subject treated with lactic acid were resensitized with IgE obtained from the serum of a patient with atopic dermatitis and stimulated by a sweat antigen (Fr.D).

A human mast cell line (LAD2: Arnold S. et al; Leukemia Research 27 (2003) 677-682) was sensitized with myeloma IgE or patient IgE and stimulated by a purified sweat antigen. As a result, as shown in FIG. 8, when sensitization was carried out with non-specific myeloma IgE as a control of human IgE, degranulation due to the stimulation by the purified sweat antigen (the degree was indicated by the release of β-hexosaminidase which is an enzyme released at the same time and at the same degree as histamine) was not observed. On the contrary, when sensitization was carried out with IgE purified from a patient with atopic dermatitis, degranulation occurred in a concentration dependent manner by a purified sweat antigen (FIG. 8). It could be confirmed that the presence of sweat antigen-specific IgE contained in the serum of a patient with atopic dermatitis can be detected from this test.

Example 8

Detection of Sweat Antigen-specific IgE in Serum Using Rat Mast Cell Line

Figure 9:
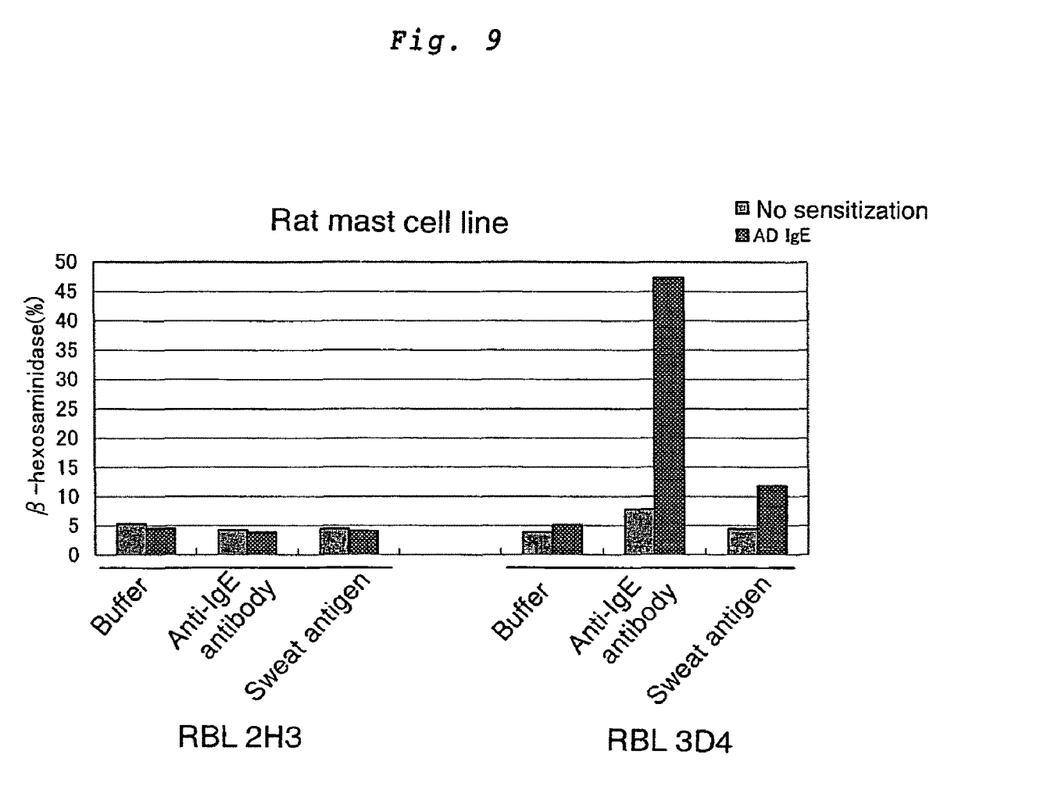
FIG. 9 shows the results of a histamine release test when a human mast cell line LAD2 was sensitized with myeloma IgE or purified IgE obtained from the serum of a patient with atopic dermatitis and stimulated by a purified sweat antigen (Fr.D). "anti-IgE antibody" indicates an anti-human IgE antibody as a control. "1/5000", "1/1500" and "1/500" indicate the dilution ratios of the purified sweat antigen (Fr.D).

An experiment was carried out using a transformant cell line RBL-3D4 prepared by using a rat mast cell line RBL-2H3 as a host and introducing a human-rat chimeric cDNA gene containing a human high affinity IgE receptor (FcεRI) α-subunit gene into the host (Hide M. et al; The Journal of Dermatology, 109: 475, 1999). In the case of the RBL-2H3 cells (the host cell line), degranulation reaction was not observed by either stimulation of the anti-IgE antibody or stimulation of the purified sweat antigen, however, in the case where RBL-3D4 cells in which a human FcεRI α-subunit was expressed were sensitized with patient IgE and stimulated by the anti-IgE antibody or the purified sweat antigen, degranulation reaction was observed in either case (FIG. 9). In the same manner as in Example 8, it could be confirmed that the presence of sweat antigen-specific IgE contained in the serum of a patient with atopic dermatitis can be detected from this test.

Example 9

Effect of Purified Sweat Antigen on Desensitization Therapy

By using the purified sweat antigen, desensitization therapy was given to 2 patients with atopic dermatitis and its effect was studied. By referring to the threshold concentration in an intradermal test, 0.5 ml of the purified sweat antigen was intradermally injected at a frequency of once per three days.

The treatment was continued while the concentration was increased to two-fold every three intradermal injections. The concentration of the antigen was increased up to about 250-fold at the maximum concentration. The therapeutic effect was determined from the reaction threshold in the intradermal test and the clinical symptoms.

In one patient, the degree of occurrence of symptoms due to the sweat was obviously reduced, and in another patient, the symptoms of atopic dermatitis were improved. A therapeutic process is shown below as one example.

Before the initiation of therapy: In a histamine release test for peripheral blood basophils using the purified sweat antigen, the histamine release rate due to the purified antigen was 59%, indicating most positive (control: 4.33%, anti-IgE antibody stimulation: 55%).

Initiation of therapy: 0.5 ml of a 12800-fold dilution of the purified sweat antigen was intradermally injected.

Continuous treatment: 0.5 ml of an antigen solution was intradermally injected while the concentration of the purified antigen was increased to two-fold every three intradermal injections. After the concentration reached 250-fold, this concentration was maintained and the treatment was continued.

The change in the threshold according to the therapeutic process is as shown in Table 1.

TABLE 1

| Desensitization therapy (Lot 1) | Threshold in intradermal test (Lot 1) |
|---|---|
| On the 9th day after the initiation of therapy | X 64 |
| On the 65th day (2nd month) after the initiation of therapy | X 32 |

As shown in Table 1, the threshold doubled on the 2nd month after the initiation of treatment, and a therapeutic effect was observed. In addition, improvement was observed in clinical findings. Thereafter, the treatment was continued, however, the purified antigen for the intradermal test was changed to Lot 2, and the therapeutic process was studied. The results are as shown in Table 2.

TABLE 2

| Desensitization therapy (Lot 2) | Threshold in intradermal test (Lot 2) |
|---|---|
| On the 75th day after the initiation of therapy | X 512 |
| On the 125th day (4th month) after the initiation of therapy | X 128 |
| On the 9th month after the initiation of therapy | X 128 |

The threshold after the 75th day after the initiation of therapy became a high value, however, the sensitivity of the patient for histamine in the intradermal test which was carried out simultaneously as a control did not change from the first treatment, therefore, it is assumed to be due to a high potency of the antigen of Lot 2. Even after changing to Lot 2, the threshold on the 125th day quadrupled, and it could be confirmed that the therapeutic effect was further increased.

Industrial Applicability

As described in detail above, by the invention of this application, an atopic dermatitis inducer produced by a patient of his or her own can be provided as a causative factor of atopic dermatitis. This makes it possible to achieve an accurate diagnosis of atopic dermatitis and a treatment of atopic dermatitis.

The invention claimed is

1. A method of purifying a human sweat fraction having basophil activation activity, which comprises:

filtering human sweat, removing insoluble matters and collecting the filtrate;

mixing the filtrate with a ConA-affinity carrier and collecting the supernatant;

fractionating the supernatant by anion exchange chromatography and/or reverse phase column chromatography;

and contacting each fraction with basophils and assaying the fractions for basophil histamine releasing activity to obtain a fraction having a histamine-releasing activity, wherein the fraction having a histamine-releasing activity has basophil activation activity, and wherein the fraction having a histamine-releasing activity does not have a basophil histamine-releasing activity after incubation with serum from a subject with atopic dermatitis but retains a basophil histamine-releasing activity after incubation with serum from a subject without atopic dermatitis at 37° C. for 30 minutes.

2. The method of claim 1, wherein the fraction having histamine releasing activity does not have basophil histamine releasing activity after incubation with 0.1 µg/µl trypsin at 37° C. for 16 hours.

* * * * *